United States Patent [19]

Sandine et al.

[11] 4,205,132
[45] May 27, 1980

[54] LYOPHILIZATION OF BACTERIA

[75] Inventors: William E. Sandine, Corvallis, Oreg.; Ebenezer R. Vedamuthu, Bradenton, Fla.

[73] Assignee: Microlife Technics, Inc., Sarasota, Fla.

[21] Appl. No.: 925,034

[22] Filed: Jul. 17, 1978

[51] Int. Cl.² ............................ C12K 1/08; C12K 3/00; A23C 19/02
[52] U.S. Cl. .................................. 435/260; 426/36; 426/43; 426/61; 426/385; 435/261; 435/885
[58] Field of Search ............... 426/34, 43, 61, 312, 426/316, 385; 195/96; 435/260, 261, 885

[56] References Cited

U.S. PATENT DOCUMENTS

| 3,592,740 | 7/1971 | Christensen | 195/96 |
| 3,897,307 | 7/1975 | Porubcan et al. | 426/61 X |
| 3,968,256 | 7/1976 | Sing | 426/43 X |
| 3,975,545 | 8/1976 | Vedamuthu | 426/43 X |

OTHER PUBLICATIONS

Speckman et al., Lyophilized Lactic Acid Starter Culture Concentrates, J. Da. Sci., vol. 57, No. 2, 1974 (pp. 165–173).

Baumann et al., Freezing of Lactic Cultures, J. Da. Sci., vol. 49, 1966 (pp. 259–264).

Cowman et al., Activity of Lactic Streptococci Following Ultra-Low-Temperature Storage, J. Da. Sci., vol. 46, 1963 (p. 609).

Douglas et al., Medium for the Propagation and Assay of Lactic and Other Phages, Laboratory Practice, vol. 23, 1974 (pp. 3–5).

Douglas, J., A Critical Review of the Use of Glycerophosphates in Microbiological Media, Laboratory Practice, vol. 20, 1971 (pp. 414–417).

Terzaghi et al., Improved Medium for Lactic Streptococci and Their Bacteriophages, Applied Microbiology, vol. 29, No. 6, 1975 (pp. 807–813).

*Primary Examiner*—David M. Naff
*Attorney, Agent, or Firm*—Ian C. McLeod

[57] ABSTRACT

Storage stable, lyophilized, acid producing bacteria, such as lactic acid bacteria, are prepared by lyophilizing the bacteria in the presence of at least 5% by weight of the bacteria of a basic organic or inorganic buffering agent, preferably an alkali metal salt of glycerophosphate, to provide lyophilized bacteria containing less than 5% by weight water, and sealing the lyophilized bacteria in a container while in a vacuum or surrounded by a gaseous atmosphere substantially free of oxygen, preferably argon which is essentially free of oxygen.

6 Claims, No Drawings

4,205,132

LYOPHILIZATION OF BACTERIA

BACKGROUND OF THE INVENTION

1. Field of the Invention

The present invention relates to a process for the lyophilization of acid producing bacteria and to the lyophilized products. In particular the present invention relates to the use of: (1) a substantial amount of an inorganic or organic buffering agent for the lyophilization; and (2) an oxygen free gaseous atmosphere or vacuum for the bacteria in order to make them storage stable.

2. Prior Art

Lyophilization or vacuum freeze-drying of heat sensitive compositions is well known to the prior art. The process is generally described in *Kirk-Othmer* Vol. 7, pages 368 and 369, (1965) and in the literature. The freezing-drying equipment used in the process includes: (1) freezing equipment; (2) a vacuum drying chamber; (3) a vacuum source; (4) an optional heat source and (5) a vapor-removal system. The ice in the frozen liquid sublimes and leaves a porous powdered composition.

Alkali metal salts of glycerophosphate have been suggested for use in enhancing the growth of bacteria by Douglas in Laboratory Practice 20: 414–417 (1971) and 23:3–5 (1974). In U.S. Pat. No. 3,975,575, one of the inventors herein described frozen concentrates of lactic acid forming bacteria incorporating an alkali metal salt of glycerophosphoric acid which have enhanced milk fermenting activity when thawed and used. In our copending application Ser. No. 649,853 filed Jan. 16, 1975 now abandoned, we described the enhancement of the milk fermenting activity of previously freeze-dried lactic acid producing bacterial cells by the addition of an alkali metal salt of glycerophosphoric acid to the freeze-dried bacteria. The glycerophosphates are used in amounts up to about five (5%) percent by weight of the bacterial concentrate. There has been no suggestion by the prior art that the salts of glycerophosphoric acid might be used for the lyophilization.

It is well known that the freeze-drying of bacteria kills most of them, usually on the order of ninety-nine percent. Those that survive die rapidly upon storage. Attempts have also been made by the prior art to increase the number of surviving bacteria upon lyophilization and storage with limited success. For instance U.S. Pat. No. 3,897,307 and an article by Speckman et al in *Journal of Dairy Science* Vol. 57, No. 2 (1973) describe such processes. Various chemical additives are used for the lyophilization and sometimes a vacuum in an attempt to increase the viability upon lyophilization and storage. Usually a storage time of at least about ninety (90) days with a significant survival of the bacteria on a percentage basis is needed for commercial purposes.

The rare gases have been generally used as a covering atmosphere to protect materials from the air or from moisture. These gases include helium, neon, krypton, and argon. Argon is derived from air and can be made essentially free of oxygen by passage of impure argon over heated copper; by selective adsorption on synthetic zeolites; or by the addition of hydrogen followed by catalytic combustion to remove oxygen and reliquefication of the argon to remove excess hydrogen. The resulting argon is 99.99 plus percent by weight pure and thus is essentially free of oxygen. It can be highly purified easily and relatively inexpensively because it is very inert in comparison to oxygen.

SUMMARY OF THE INVENTION

Objects

It is therefore an object of the present invention to provide a process for preparing storage stable lyophilized bacterial compositions. It is further an object of the present invention to provide a lyophilization process which produces a high level of survival of the bacteria upon lyophilization. These and other objects will become increasingly apparent by reference to the following description.

General Description

The present invention relates to the storage stable lyophilized bacterial product which comprises: (a) acid producing bacteria which have been lyophilized in the presence of at least above five percent (5%) based upon the wet weight of the bacteria of a non-toxic, water soluble, inorganic or organic basic buffering agent so as to be viable and contain less than about five percent (5%) by weight moisture; and (b) a gaseous atmosphere which is inert to the bacteria which is substantially free of oxygen or a vacuum provided in a sealed container with the bacteria, wherein at least about ten percent (10%) of the bacteria surviving lyophilization remain viable for 90 days. It also relates to the method of producing a storage stable lyophilized bacterial product which comprises: (a) providing acid producing bacteria mixed with at least about five percent (5%) based upon the weight of the bacteria of a non-toxic, water soluble, inorganic or organic basic buffering agent so that the bacteria are viable in an aqueous medium; (b) rapidly freezing the bacteria in a sealable container; (c) lyophilizing the bacteria with a vacuum in a sealed chamber to remove water wherein the bacteria contain less than above five percent (5%) by weight water as a result of lyophilization; and (d) surrounding the bacteria with a gaseous atmosphere which is substantially free of oxygen or a vacuum and then sealing the container, wherein at least about ten percent (10%) of the bacteria surviving lyophilization remain viable for ninety (90) days.

It is well known that lyophilization of acid producing bacteria causes large numbers of the bacteria to die or at least to be severely impaired in their ability to function. It is also well known that the acids which the bacteria produce are toxic to the bacteria and will eventually kill them. In their weakened condition, particularly when the lyophilized bacteria are at refrigeration temperatures or above, it is believed that the bacteria still are able to generate acids which damage and eventually kill the weakened bacteria upon storage for even a few days. Without the ability to ship or store the lyophilized bacteria and to provide for the survival of at least about ten percent (10%) of the bacteria surviving lyophilization over a period of ninety (90) days, the lyophilized products are not commercially useful. The problem of developed acidity is compounded because the bacteria are also sensitive to the atmosphere under which they are stored.

Unexpectedly, it has been discovered that by combining lyophilization in the presence of at least about five percent (5%) based upon the wet weight of the bacteria of a water soluble non-toxic, inorganic or organic basic buffering agent and a non-reactive gaseous atmosphere substantially free of oxygen or a vacuum, the resulting bacteria are storage stable. The pH of the agent when used at 5% level in milk before adding the bacteria is preferably between about 7.2 and 7.4. Generally the pH is between about 6 and 8. The resulting products are relatively storage stable over a period of at least about ninety (90) days and preferably at least about 180 days and remain more viable than by any other known lyophilization method.

The gaseous atmosphere can be a relatively inert gas which is substantially free of oxygen. The rare gases, neon, argon, helium, and krypton can be used at various pressures including a partial vacuum. Argon is preferred because it is inexpensive in oxygen free form. A full vacuum of less than about 50 millitorr can be used since it is substantially oxygen free, but is not preferred since it is difficult to maintain.

The bacteria are provided in a container with the vacuum or the gaseous atmosphere. Preferably they are stored and transported at 12.8° C. to −10° C. although some Streptococcae strains can survive at ambient temperatures for over ninety (90) days.

Detailed Description

The preferred acid producing bacteria which are lyophilized are those which are milk fermenting to produce lactic acid and other flavors in cultured milk products and are included in the families Streptococcaceae, Lactobacillaceae, comprising the genera Steptococcus, Leucomostoc and Lactobacillus. Representative members are *Streptococcus lactis* and *Streptococcus lactis* subsp. *diacetylactis, Streptococcus cremoris, Streptococcus thermophilus,* Leuconostoc spp., *Lactobacillus bulgaricus, Lactobacillus acidophilus* and *Lactobacillus lactis.* The lactic acid bacteria can be combined with so called "aroma" forming bacteria of the genus Leuconostoc, in particular *Leuconostoc citrovorum* (now known as *Leuconostoc cremoris*) or *Leuconostoc dextranicum* used in making buttermilk. Other lactic acid producing bacteria include those used for making fermented meat products and pickles such as *Pediococcus cerevisiae* and *Lactobacillus plantarum* and mixtures thereof as well as members of the family Micrococcaceae. The classifications are as defined in Bergey's Manual, Eighth Edition (1974). Other acid producing bacteria which can be freeze-dried by the method of the present invention to improve the yield of live bacteria, are vinegar (acetic acid) and citric acid producing bacteria. Acid producing bacteria have a wide variety of commercial uses other than for food products as is well known in the patent art.

The bacteria are lyophilized in the presence of at least about five percent (5%) by weight of the bacteria of an inorganic or organic non-toxic basic buffering agent. The preferred buffering agent is an alkali metal salt of glycerophosphoric acid which provides a buffered pH of about 7.2 when combined with the bacteria. Other buffering systems are described in *Lange's Handbook of Chemistry,* McGraw-Hill (10th Ed 1967) at pages 971 and 972. The preferred buffering agents do not volatilize in a vacuum upon lyophilization.

The growth and concentration of bacteria is well known to the prior art. In general the bacteria are grown in a suitable growth medium including water. The alkali metal salts of glycerophosphoric acid can be used for this purpose as described by Douglas et al.

Prior to lyophilization, the bacteria are in admixture with amounts of water and growth media and usually there are at least about $10^8$ up to about $10^{15}$ cells per ml, preferably between about $10^9$ to $10^{12}$ cells per ml in water. The lactic acid producing species of bacteria are preferably grown in non-fat dry milk or a milk digest and a small amount is added to the bacteria during and after lyophilization. The bacteria are maintained at a pH between about 6.0 and 6.5 during growth to prevent lactic acid damage of the bacteria.

Cell growth can be used to produce concentrations of between about $10^8$ to $10^{10}$ cells per ml. Centrifuging, reverse osmosis and dialysis are known methods of increasing the concentration of cells up to about $10^{15}$ cells per ml. For purposes of lyophilization, the more concentrated the cells, the less liquid (primarily water) which has to be removed. Preferably the cells are frozen to less than minus −78° C. for lyophilization. A vacuum of less than about 50 millitorr is also preferred for the lyophilization.

The wet bacterial cells are frozen in admixture with an effective amount of the buffering agent which is non-toxic to the bacteria, preferably an alkali metal salt of glycerophosphoric acid, which is at least about five percent (5%) by weight of the combination of the bacteria with the water and the growth medium. Usually this amount produces between at least about 50 to 60 parts by weight of the basic buffering per 100 parts of the powdered lyophilized product. Unexpectedly it has been found that the basic buffering agents, particularly alkali metal salts of glycerophosphoric acid, significantly increase the survival of the bacteria upon lyophilization. The useful alkali metal salts of glycerophosphoric acid are principally sodium and potassium. The preferred salt is sodium in the form of the beta isomer.

In the preferred process, the bacteria are first frozen in the presence of the alkali metal salts of glycerophosphoric acid in the manner of U.S. Pat. No. 3,975,545 and then, in a conventional lyophilization, subjected to a vacuum, in order to cause the frozen liquid (principally water) to sublime. The bacteria prior to freezing should not contain materials which prevent effective lyophilization to a dry, flowable powder. For instance, glycerol, described in U.S. Pat. No. 3,975,545 as a stabilizing agent for freezing, is not suitable since it is a liquid which prevents lyophilization and produces a gum.

The bacteria which are best adapted to the process of the present invention are those which are used to produce lactic acid in milk for cheese making and the like, since they are very sensitive to freeze-drying. In some instances the bacteria cannot be freeze-dried at all and thus sensitivity needs to be determined initially. The process is also particularly useful for meat fermenting bacteria which are relatively quite hardy. The following are specific Examples of the present invention.

EXAMPLE 1

Bacteria were grown in 700 ml of an aqueous medium including lactose, yeast extract, tryptone, at 30° C. with pH maintenance (at pH 6.4) until the lactose was exhausted (about 15 hrs). The product is referred to as "fermenter cells". The cell count was $1.1 \times 10^{10}$ colony forming units (cfu/ml).

The activity (acidity) on the fermenter medium was done after diluting the medium 1:10. The diluted cells were inoculated at a one percent (1%) by weight level into previously steamed non-fat milk (NFM) and incubated at 30° C. for 6 hrs and then titrated with sodium hydroxide to determine the acidity.

Fermenter cells (600 ml) were harvested in two 300 ml batches. One batch was resuspended in 30 ml of 11% by weight nonfat milk (NFM) and the other in 30 ml of 11% NFM containing 15% by weight sodium beta glycerophosphate (GP). Two ml (2 ml) aliquots were freeze-dried and sealed in vials under vacuum for storage at 25° C. The vial contents were rehydrated with 2.0 ml of sterile NFM, diluted 1:10 in NFM and the activity measured by inoculating the diluted concentrate (1.0 ml) into 100 ml of NFM or NFM+2% GP as with the fermenter cells and determining the titratable acidity with sodium hydroxide as a function of time. The diluted lyophilized concentrates had the following cell counts: $7.4 \times 10^9$ cfu/ml in NFM for 67.2% survival and $7.5 \times 10^9$ cfu/ml in NFM+15% GP for 68.2% survival.

The following Table shows the results where a vacuum was used to store the lyophilized bacteria for various periods of time.

TABLE 1

Activity of Fermenter Cells and Lyophilized Concentrates of Strain H1 at Zero Time.

| | Fermenter Cells | | Lyophilized Concentrate | | | | | |
|---|---|---|---|---|---|---|---|---|
| | | | NFM | | | | NFM + 15% GP | |
| | | | NFM | | NFM + 2% GP | | NFM | NFM + 2% GP |
| Hours | pH | TA | pH | TA | pH | TA | pH | TA | pH | TA |
| 1 | 6.3 | .15 | 6.3 | .12 | 6.8 | .17 | 6.5 | .19 | 7.4 | .19 |
| 2 | 5.5 | .37 | 6.1 | .22 | 7.0 | .19 | 6.5 | .21 | 7.2 | .21 |
| 3 | 5.5 | .38 | 6.1 | .27 | 7.1 | .26 | 6.0 | .26 | 7.0 | .25 |
| 4 | 5.2 | .53 | 5.4 | .40 | 6.6 | .38 | 5.4 | .35 | 6.7 | .32 |
| 5 | 4.4 | .70 | 4.8 | .56 | 5.8 | .42 | 4.8 | .55 | 5.9 | .53 |
| 6 | 4.2 | .78 | 4.4 | .72 | 5.4 | .72 | 4.7 | .71 | 5.7 | .78 |

NFM - Nonfat milk
GP - Sodium beta glycerophosphate
TA - Titratable acidity

TABLE 1-1

Activity of Lyophilized Concentrates of Strain H1 at 30 days[a]

| | NFM | | NFM + 15% GP | |
|---|---|---|---|---|
| Hours | pH | TA | pH | TA |
| 1 | 6.5 | .18 | 6.6 | .18 |
| 2 | 6.4 | .19 | 6.4 | .19 |
| 3 | 6.4 | .21 | 6.3 | .22 |
| 4 | 6.2 | .22 | 5.7 | .32 |
| 5 | 6.2 | .21 | 5.4 | .40 |
| 6 | 6.1 | .23 | 4.8 | .56 |
| 7 | — | — | 4.6 | .66 |

[a]Cell counts of 1:10 diluted concentrates were $< 10^7$ in NFM for $<0.09$ survival and $5.0 \times 10^9$ in NFM + 15% GP for 45.5% survival.

TABLE 1-2

Activity of Lyophilized Concentrates of Strain H1 at 60 days

| | 11% NFM | | 11% NFM + 15% GP | |
|---|---|---|---|---|
| Hours | pH | TA | pH | TA |
| 1 | 6.5 | .20 | 6.5 | .19 |
| 2 | 6.4 | .22 | 6.4 | .21 |
| 3 | 6.3 | .22 | 6.3 | .22 |
| 4 | 6.2 | .22 | 6.3 | .22 |
| 5 | 6.2 | .22 | 6.2 | .23 |
| 6 | 6.0 | .23 | 6.4 | .20 |

Cell counts on 1:10 diluted concentrates were $< 10^7$ in NFM for $<0.09\%$ survival, and $4.8 \times 10^9$ in 15% GP for 43.6% survival. The vials had no vacuum.

TABLE 1-3

Activity of Lyophilized Concentrates of Strain H1 at 90 days

| | 11% NFM | | NFM + 15% GP | |
|---|---|---|---|---|
| Hours | pH | TA | pH | TA |
| 1 | 6.6 | .20 | 6.7 | .20 |

TABLE 1-3-continued

Activity of Lyophilized Concentrates of Strain H1 at 90 days

| | 11% NFM | | NFM + 15% GP | |
|---|---|---|---|---|
| Hours | pH | TA | pH | TA |
| 2 | 6.6 | .20 | 6.6 | .20 |
| 3 | 6.5 | .20 | 6.6 | .20 |
| 4 | 6.5 | .24 | 6.4 | .22 |
| 5 | 6.3 | .21 | 6.4 | .25 |
| 6 | 6.3 | .22 | 6.3 | .24 |

Diluted cell counts were $< 10^7$ in NFM and $3.2 \times 10^9$ in GP for 29% survival.

EXAMPLE 2

The following Table 2 shows the results where oxygen free argon was used to store the lyophilized bacteria for various periods of time.

TABLE 2

Activity of Fermenter Cells and Lyophilized Concentrates of Strain H1 at Zero Time Under Argon

| | Fermenter Cells | | Lyophilized Concentrate[b] | | | |
|---|---|---|---|---|---|---|
| | | | NFM | | NFM + 15% GP | |
| Hours | pH | TA | pH | TA | pH | TA |
| 1 | 6.4 | .26 | 6.5 | .18 | 6.6 | .19 |
| 2 | 5.9 | .28 | 6.2 | .20 | 6.4 | .21 |
| 3 | 5.4 | .38 | 5.9 | .26 | 6.0 | .27 |
| 4 | 4.4 | .68 | 5.1 | .48 | 5.1 | .48 |
| 5 | 5.2 | .74 | 4.7 | .59 | 4.7 | .61 |
| 6 | 4.0 | .75 | 4.4 | .76 | 4.4 | .75 |

[a]pH control was set at 6.4 and was 6.2 when cells were harvested and 40 ml of 10 N NH$_4$OH was used. The cell count was $1.7 \times 10^{10}$.
[b]Diluted dry concentrate had following cell counts: $1.3 \times 10^{10}$ cfu/ml in NFM for 76.5% survival and $1.2 \times 10^{10}$ cfu/ml in NFM + 15% GP for 70.6% survival.

TABLE 2-1

Activity of Lyophilized Concentrates of Strain H1 at 2 Weeks under Argon

| | NFM | | | | 15% GP | | | |
|---|---|---|---|---|---|---|---|---|
| | Sample 1 | | Sample 2 | | Sample 1 | | Sample 2 | |
| Hours | pH | TA | pH | TA | pH | TA | pH | TA |
| 1 | 6.7 | .18 | 6.5 | .19 | 6.6 | .19 | 6.5 | .19 |
| 2 | 6.7 | .18 | 6.5 | .18 | 6.6 | .20 | 6.5 | .19 |
| 3 | 6.4 | .20 | 6.4 | .20 | 6.0 | .27 | 6.0 | .26 |
| 4 | 6.4 | .20 | 6.4 | .20 | 5.6 | .39 | 5.6 | .39 |
| 5 | 6.4 | .20 | 6.4 | .20 | 5.2 | .50 | 5.2 | .52 |
| 6 | 6.4 | .20 | 6.4 | .20 | 4.7 | .73 | 4.8 | .66 |

Cell counts of 1:10 diluted concentrates were $1.0 \times 10^8$ cfu/ml in NFM for 0.6% survival, and $1.52 \times 10^{10}$ in 15% GP for 88% survival.

TABLE 2-2

Activity of Lyophilized Concentrates of Strain H1 at 30 Days under Argon

| | NFM | | 15% GP | |
|---|---|---|---|---|
| Hours | pH | TA | pH | TA |
| 1 | 6.5 | .19 | 6.3 | .22 |
| 2 | 6.4 | .19 | 6.0 | .25 |
| 3 | 6.4 | .20 | 5.9 | .30 |
| 4 | 6.3 | .21 | 5.9 | .34 |
| 5 | 6.3 | .21 | 5.2 | .53 |
| 6 | 6.3 | .25 | 4.7 | .70 |

Cell counts of 1:10 diluted concentrates were $4.0 \times 10^8$ cfu/ml in NFM for 2% survival, and $1.06 \times 10^{10}$ for 62% survival.

TABLE 2-3

Activity of Lyophilized Concentrates of Strain H1 at 60 Days under Argon[a]

| | NFM | | 15% GP | |
|---|---|---|---|---|
| Hours | pH | TA | pH | TA |
| 1 | 6.7 | .20 | 6.7 | .19 |
| 2 | 6.6 | .25 | 6.5 | .23 |

TABLE 2-3-continued
Activity of Lyophilized Concentrates of Strain H1 at 60 Days under Argon[a]

| Hours | NFM pH | NFM TA | 15% GP pH | 15% GP TA |
|---|---|---|---|---|
| 3 | 6.3 | .25 | 6.2 | .26 |
| 4 | 6.3 | .25 | 5.8 | .35 |
| 5 | 6.0 | .25 | 5.4 | .49 |
| 6 | 6.0 | .25 | 5.7 | .59 |

[a]Diluted dry concentrates had following counts: 1.4 × 10⁹ in NFM for 8.2% survival, and 5.8 × 10⁹ in 15% GP for 34% survival.

TABLE 2-4
Activity Test of Lyophilized Concentrates at 90 Days Under Argon[a].

| Hours | 11% NFM pH | 11% NFM TA | 15% GP pH | 15% GP TA |
|---|---|---|---|---|
| 1 | 6.4 | .18 | 6.4 | .17 |
| 2 | 6.4 | .18 | 6.4 | .18 |
| 3 | 6.3 | .18 | 6.4 | .18 |
| 4 | 6.3 | .18 | 5.9 | .28 |
| 5 | 6.3 | .19 | 5.7 | .38 |
| 6 | 6.3 | .20 | 5.4 | .40 |

[a]Diluted dry concentrates had following counts: no apparent survival in NFM and 5.1 × 10⁹ in 15% GP for 30% survival.

The data for *Streptococcus lactis* H1 in Example 2 shows that lyophilization of cell concentrates ($10^{10}$ cells/ml) in the presence of 15% sodium beta glycerophosphate (GP), sealing under vacuum and storage under argon gas yields active lyophilized concentrates. Typical activity and survival data were as shown in Table 3.

TABLE 3

| Days of Storage | Activity[a b] C[c] | Activity[a b] E[d] | % Survival C | % Survival E |
|---|---|---|---|---|
| 0 | .76 | .75 | 77 | 71 |
| 15 | .20 | .66 | 1 | 88 |
| 30 | .25 | .70 | 2 | 62 |
| 60 | .25 | .59 | 8 | 34 |
| 90 | .20 | .40 | 1 | 30 |

[a]Titratable acidity after 6 hr at 30° C.
[b]Under argon at 25° C.
[c]C = Control, 11% nonfat milk (NFM)
[d]E = NFM + 15% GP It was also found that cells exposed to oxygen briefly and then re-vacuumized died off rapidly, emphasizing the critical importance of preventing oxygen contact with the bacteria.

EXAMPLE 3

The experimental procedures were essentially the same as given in Examples 1 and 2. Nine additional single strains were tested to see if suitable lyophilized products could be prepared. All except *S. lactis* ML-8 and *S. cremoris* P₂ were unsatisfactory, revealing essentially no activity when tested the day after lyophilization (zero time storage). For *S. lactis* the lyophilized product showed 0.41% acid (pH 5.1) in the 6 hour activity test even after 6 months of storage under a vacuum at room temperatures and *S. cremoris* was similar.

It appeared from Example 3 that strain selection was important to the lyophilized products.

The products were tested without diluting them 1:10 in NFM after rehydration as had been done in Examples 1 and 2. The activity tests were made after incubation for 12 hours at 22° C. If the lyophilized products were active under these conditions, this allows their use in direct set bulk starters. A mixture of *S. lactis* and *S. cremoris* was lyophilized. Data typical of what was obtained for this mixed culture were as follows as shown in Table 4.

TABLE 4

| Days of Storage | Activity 6 hours at 30° C. pH | Activity 6 hours at 30° C. TA | Activity 12 hours at 22° C. pH | Activity 12 hours at 22° C. TA |
|---|---|---|---|---|
| 0 | 4.8 | .68 | 4.5 | .96 |
| 14 | 4.8 | .76 | 4.7 | .83 |

The results show that the mixture could be used in direct set starters.

EXAMPLE 4

Data for two other lyophilized bacterial strains of *S. lactis* which produced similar results to H1 were:

| Days of Storage | Activity - 6 hours at 30° C. Strain 1 pH | Strain 1 TA | Strain 2 pH | Strain 2 TA |
|---|---|---|---|---|
| 0 | 4.2 | .73 | 4.1 | .79 |
| 14 | 4.5 | .72 | — | — |
| 30 | — | — | 4.6 | .79 |
| 90 | — | — | 4.7 | .80 |
| 100 | 4.7 | .77 | — | — |

EXAMPLE 5

An experiment was run with the mixed *S. lactis* and *S. cremoris* to compare the influence of water, NFM, 5% GP and 10% GP as lyophilization menstra on the activity (6 hours at 30° C.) of resulting lyophilized product. The following data were obtained as shown in Table 5.

TABLE 5

| Days of Storage | H₂O pH | H₂O TA | H₂O % S | NFM pH | NFM TA | NFM % S | 5% GP pH | 5% GP TA | 5% GP % S | 10% GP pH | 10% GP TA | 10% GP % S |
|---|---|---|---|---|---|---|---|---|---|---|---|---|
| 0 | 5.0 | .58 | 76 | 4.4 | .76 | 95 | 4.4 | .74 | 100 | 4.4 | .78 | 100 |
| 14 | 5.0 | .42 | 35 | 5.3 | .50 | 24 | 4.9 | .70 | 47 | 4.9 | .68 | 75 |
| 30 | 6.2 | .31 | 0.04 | 5.3 | .54 | 0.05 | 5.0 | .61 | 11 | 5.0 | .67 | 24 |

% S = % Survival

These data clearly show that GP is effective as a protectve agent and that 10% is much better than 5%.

EXAMPLE 6

Experiments were run to evaluate the possible interactive effects of the argon and vacuum storage conditions. Four treatment conditions were used, argon storage without vacuum, (A+V−); argon storage with vials sealed under vacuum, (A+V+); no argon or vacuum, (A−V−) and no argon but vials vacuum sealed (A−V+). Reslts obtained with the mixed *S. lactis* and *S. cremoris* were as shown in Table 6.

TABLE 6

| Days of Storage | A+V- pH | A+V- TA | A+V- % S | A+V+ pH | A+V+ TA | A+V+ % S | A-V- pH | A-V- TA | A-V- % S | A-V+ pH | A-V+ TA | A-V+ % S |
|---|---|---|---|---|---|---|---|---|---|---|---|---|
| 0 | 4.8 | .79 | 100 | 4.8 | .79 | 100 | 4.8 | .79 | 100 | 4.8 | .79 | 100 |
| 14 | 5.2 | .51 | — | 4.8 | .71 | 67 | 5.3 | .60 | 18 | 4.9 | .68 | 57 |
| 30 | 5.0 | .69 | — | 4.8 | .74 | — | 6.0 | .32 | — | 4.8 | .70 | — |

From these data it appears that the best lyophilized product performance is achieved when both vacuum and argon storage conditions are used. The lyophilized products have sufficient activity after 30 to 60 days of storage at ambient temperatures and much longer if refrigerated to directly inoculate bulk starter milk.

We claim:

1. The method of producing a storage stable lyophilized bacterial product which comprises:
   (a) providing acid producing bacteria mixed with a lyophilizing composition consisting essentially of at least about five percent by weight of the bacteria of an alkali metal glycerophosphate as a buffering agent in an aqueous medium including milk solids which has a pH between about 6 and 8 without the bacteria;
   (b) rapidly freezing the bacteria in a sealable container;
   (c) lyophilizing the bacteria with a vacuum in a sealed chamber to remove water wherein the bacteria contain less than five percent by weight water as a result of lyophilization; and
   (d) surrounding the bacteria with argon which is essentially free of oxygen and sealing the container, wherein at least about ten percent of the bacteria surviving lyophilization remain viable for 90 days.

2. The method of claim 1 wherein the bacteria are lactic acid producing.

3. The method of claim 1 wherein the alkali metal glycerophosphate is sodium beta glycerophosphate.

4. The method of claim 1 wherein the acid producing bacteria are frozen in the sealable container to less than about minus 78° C. for lyophilization.

5. The method of claim 4 wherein the lyophilization is in a vacuum of less than about 50 millitorr.

6. The storage stable eyophilized bacterial product of the method of claim 1.

* * * * *

UNITED STATES PATENT AND TRADEMARK OFFICE
CERTIFICATE OF CORRECTION

PATENT NO. : 4,205,132
DATED : May 27, 1980
INVENTOR(S) : William E. Sandine and Ebenezer R. Vedamuthu It is certified that error appears in the above-identified patent and that said Letters Patent are hereby corrected as shown below:

Column 1, line 32, "1975" should be --1976--.

Column 6, line 28, Table 2 (Hour 5) "5.2" should be --4.2--.

Column 7, line 9, Table 2-3 (Hour 6) "5.7" should be --5.0--.

Column 8, line 67, "reslts" should be --results--.

Column 10, line 28, "eyophilized" should be --lyophilized--.

Signed and Sealed this

Ninth Day of September 1980

[SEAL]

Attest:

SIDNEY A. DIAMOND

Attesting Officer

Commissioner of Patents and Trademarks